United States Patent
Schodel et al.

(10) Patent No.: US 9,139,492 B2
(45) Date of Patent: *Sep. 22, 2015

(54) METHOD FOR PROCESSING COKE OVEN GAS

(75) Inventors: Nicole Schodel, Munich (DE); Ernst Haidegger, Riemerling (DE); Holger Schmigalle, Wolfratshausen (DE); Volker Goke, Geretsried (DE); Harald Schmaderer, Wolfratshausen (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/344,933

(22) PCT Filed: Aug. 7, 2012

(86) PCT No.: PCT/EP2012/003370
§ 371 (c)(1),
(2), (4) Date: Sep. 2, 2014

(87) PCT Pub. No.: WO2013/037443
PCT Pub. Date: Mar. 21, 2013

(65) Prior Publication Data
US 2015/0044129 A1 Feb. 12, 2015

(30) Foreign Application Priority Data

Sep. 15, 2011 (DE) .......................... 10 2011 113 504
Nov. 17, 2011 (EP) ..................................... 11009117

(51) Int. Cl.
| C07C 41/09 | (2006.01) |
| C07C 11/02 | (2006.01) |
| C07C 1/22  | (2006.01) |
| F27D 17/00 | (2006.01) |
| C07C 41/01 | (2006.01) |
| C07C 1/20  | (2006.01) |
| C01B 3/50  | (2006.01) |
| C07C 5/09  | (2006.01) |

(52) U.S. Cl.
CPC . *C07C 1/22* (2013.01); *C01B 3/506* (2013.01); *C07C 1/20* (2013.01); *C07C 5/09* (2013.01); *C07C 41/01* (2013.01); *F27D 17/008* (2013.01); *C01B 2203/046* (2013.01)

(58) Field of Classification Search
CPC ................................ C07C 41/09; C07C 11/02

USPC .................................. 568/698; 585/254, 639
See application file for complete search history.

(56) References Cited

U.S. PATENT DOCUMENTS

2011/0112314 A1   5/2011   Chewter et al.

FOREIGN PATENT DOCUMENTS

| CN | 101096331 A | 1/2008 |
| CN | 101659879 A | 3/2010 |
| CN | 101823937 A | 9/2010 |
| JP | 4346950 A  | 12/1992 |

OTHER PUBLICATIONS

International Search Report dated Nov. 5, 2012 issued in corresponding PCT/EP2012/003370 application (pp. 1-2).
English Translation Abstract of CN 101823937 published Sep. 8, 2010.
Search Report and English translation of First Office Action in Chinese Patent Applications No. 201280045013 issued on Apr. 24, 2015.
English Translation Abstract of CN 101096331 published Jan. 2, 2008.
English Translation Abstract of JP4346950A published Dec. 2, 1992.
English Translation Abstract of CN 101659879 published Mar. 3, 2010.
Cai Guangyu et al; Natural Gas Chemical Industry, vol. 19, No. 5, pp. 26-30 published Oct. 30, 1994.

*Primary Examiner* — Sikarl Witherspoon
(74) *Attorney, Agent, or Firm* — Millen, White, Zelano & Branigan, P.C.

(57) ABSTRACT

The invention relates to a method for processing coke oven gas, said coke oven gas containing hydrogen, wherein the coke oven gas is at least partially integrated into a method for producing dimethyl ether in conjunction with a gas containing carbon monoxide and/or carbon dioxide, whereby a DME-containing product gas is formed. At the outset of the method for the formation of dimethyl ether, a ratio of hydrogen to carbon monoxide, weighted with the carbon dioxide concentration (formula (I)), of 0.9 to 1.1 is set, wherein the DME-containing product gas is integrated into a method for converting dimethyl ether to olefins, whereby an olefin-containing product gas is formed, and wherein olefins, in particular ethylene and/or propylene, is/are separated from the olefin-containing product gas by means of separating methods.

$$\frac{c[H2] - c[CO2]}{c[CO] + c[CO2]} \qquad (I)$$

12 Claims, No Drawings

METHOD FOR PROCESSING COKE OVEN GAS

The invention relates to a process for processing offgas from a coking plant, where the offgas contains hydrogen.

In a coking plant, coke is produced from coal in a coke oven. Here, the volatile constituents in the coal are pyrolyzed by heating to a temperature of from 900° C. to 1400° C. in a coke oven, liberated and extracted. This forms the coke which consists essentially of carbon and an offgas which contains the volatile constituents and is referred to as coking plant gas. The pyrolysis in the coke oven takes place in the absence of oxygen. This is in principle a batch process, and the composition of the coking plant offgas liberated fluctuates. However, since a plurality of coke collectors are always operated, the average gas composition is subjected to only small fluctuations: the coking plant gas formed contains hydrogen (about 55%), methane, nitrogen, carbon monoxide, carbon dioxide, sulfur and higher hydrocarbons.

WO2009023987, CN 101 913 558, CN 101 823 937 and CN 102 079 689 disclose processes for preparing methanol or dimethyl ether from coking plant offgas and from offgas obtained in steel production.

US 2011/0112314 comprises a process for preparing olefins from oxygen-containing feedstocks.

It is an object of the present invention to obtain one or more products of value from the offgas from a coking plant.

This object is achieved by the offgas being at least partly fed together with a gas containing carbon monoxide and/or dioxide to a process for forming methanol and/or dimethyl ether, as a result of which a DME-containing product gas is formed, the DME-containing product gas is fed to a process for converting dimethyl ether to olefins as a result of which an olefin-containing product gas is formed, and olefins, in particular ethylene and/or propylene, are separated off from the olefin-containing product gas by means of a separation process.

Furthermore, according to the invention, a ratio of hydrogen to carbon monoxide weighted by the carbon dioxide concentration $$\frac{c[H2] - c[CO2]}{c[CO] + c[CO2]}$$

of from 0.9 to 1.1, preferably 1, is set at the inlet of the process for forming dimethyl ether and dimethyl ether is formed. Carbon dioxide is advantageously also formed from carbon monoxide.

Here, the hydrogen content is regulated in such a way that the reaction proceeds selectively for dimethyl ether, depending on the further specific process (catalyst, etc.) for the formation of olefins, in particular ethylene.

The basic concept of the invention is to produce a type of synthesis gas from the hydrogen-containing offgas from the coke oven of a coking plant and convert this into valuable olefin products. The olefins can be separated off from the olefin-containing product gas by means of known separation processes. In particular, the olefin-containing product gas can simply be fed as feed into the fractionation part of an olefin plant. The present invention is particularly worthwhile at sites where inexpensive gas containing carbon monoxide and/or carbon dioxide is economically available.

Processes for converting, for example, methanol into olefins (e.g. production of ethylene by catalytic dehydrogenation of methanol over aluminum and zeolite catalysts) are known in the prior art and are described, for example, in "Ethylene", H. Zimmerman and R. Walzl in *Ullmann's Encyclopedia of Industrial Chemistry*, Wiley 2011. The same applies to the isolation of olefins, in particular ethylene and propylene, from such olefin-containing streams (see same reference and references present therein). The present invention is not limited to the processes described there and the separation processes described there.

In a preferred embodiment of the invention, offgas from a blast furnace and/or converter of a steelworks or a smelting works is used as gas-containing carbon monoxide and/or carbon dioxide. Coking plants are frequently located in the vicinity of steelworks or smelting works since coke is required in large quantities in the blast furnaces of such works. Large amounts of offgases containing carbon monoxide and/or carbon dioxide are formed in these works, for example, in the blast furnaces themselves or in the converters. In this embodiment of the invention, the advantages of the present invention are particularly evident since here the offgases from the two works are converted into products of value.

Offgases from a direct reduction process for iron ore are particularly suitable for the process of the invention. Offgases from the direct reduction process for iron ore contain carbon monoxide and hydrogen in a ratio which is very particularly suitable for preparing dimethyl ether.

In an embodiment of the invention, offgas and/or the gas containing carbon monoxide and/or carbon dioxide are purified before the two are fed as feed to the process for forming methanol and/or dimethyl ether. Here, for example, all constituents except for carbon monoxide and/or carbon dioxide can be removed from the gas containing carbon monoxide and/or carbon dioxide. After the purification, the offgas advantageously consists of only hydrogen and optionally carbon monoxide and/or carbon dioxide.

The olefin-containing product gas is, after separating off the olefins, advantageously recirculated as alkane-containing tail gas for bottom firing to the coke oven and/or blast furnace. A small proportion of hydrocarbons (mainly alkanes) are firstly present in the offgases from the furnaces, and secondly alkanes are also formed in secondary reactions in olefin formation. After the olefins, in particular ethylene and/or propylene, have been separated off from the olefin-containing product gas, the alkane-containing tail gas now consists mainly of alkanes and other combustible constituents. It is therefore very well suited for bottom firing of the furnaces (coke oven and/or blast furnace).

In an embodiment, methane is separated off from the alkane-containing coke gas and fed as feed into a gas turbine for generating electric energy. This embodiment of the invention combines the invention with the prior art in which the offgas is used mainly for generating electric energy. Among the constituents of the offgas, methane is best suited for use in a gas turbine for generating electric energy and is, in this embodiment of the invention, separated off from the alkane-containing tail gas and introduced as feed into a gas turbine or fed into an existing natural gas grid.

In an alternative embodiment of the invention, a fraction containing hydrocarbons having not more than one carbon atom is separated off from the DME-containing product gas after the process for forming dimethyl ether. This fraction consists essentially of methane in this embodiment of the invention.

Hydrogen is advantageously separated off from the olefin-containing product gas by means of a cryogenic separation process. If the olefin-containing product gas still contains hydrogen which has not been reacted in the preceding process steps, this is automatically separated off in the cryogenic separation sequence (for example when the olefin-containing product gas is fed into an existing olefin plant or else in a separate separation sequence) and can be used as product elsewhere in the plant or be discharged.

In a further embodiment of the invention, the alkane-containing tail gas is fed into a process for the partial oxidation of alkanes to alkenes and alkynes in the presence of oxygen, forming an oxidation product gas which is recirculated to the separation process for separating off the olefins. The hydrogen and the oxidation product gas are advantageously fed to a process for the catalytic hydrogenation of alkynes, as a result of which a hydrogenation product gas is formed and the hydrogenation product gas is recirculated to the separation process for separating off the olefins.

The recycle streams described likewise contain olefins, in particular ethylene and/or propylene, which further increase the ethylene and/or propylene yield and thus improve the economics.

In another embodiment of the invention, the alkane-containing tail gas is fed into a thermal process in the absence of oxygen, as a result of which a pyrolysis product gas and carbon are formed, and the pyrolysis product gas is fed into a pressure swing absorption process where it is separated into hydrogen and an acetylene-containing tail gas. The acetylene-containing tail gas consists very predominantly of acetylene which can be discharged as product of value or used as fuel in the plant. Apart from the use of a pressure swing absorption process, alternative processes with which a person skilled in the art will be familiar, e.g. membrane separation processes or, particularly in the case of relatively high acetylene content, chemical scrubbing comprising at least one scrubbing and regeneration stage, are also conceivable.

In a further embodiment of the invention, the coking plant offgas is fed into a process for reforming methane to form carbon monoxide upstream of the process for forming methanol and/or dimethyl ether, forming a reformer product gas. In this embodiment of the invention, the carbon monoxide content at the inlet to the process for forming methanol and/or dimethyl ether is increased and formation of the product of this process is thus promoted. Thus, more olefins, in particular ethylene and/or propylene can be formed in the subsequent process step. In addition, the proportion of methane in the olefin-containing product gas becomes smaller and the isolation of the olefins, in particular ethylene and/or propylene is thus simplified. In an alternative embodiment, the reformer can be combined with a water gas shift reactor.

The alkane-containing tail gas can likewise be recirculated together with the offgas to the process for reforming methane in order to increase the carbon monoxide content upstream of the process for forming methanol and/or dimethyl ether.

The present invention makes it possible, in particular, to convert coking plant offgases into products of value. The offgas is thus not released into the atmosphere and pollution of the environment is reduced.

The invention claimed is:
1. A process for processing offgas from a coking plant, where the offgas contains hydrogen, said process comprising:
at least partly feeding said offgas, together with a gas containing carbon monoxide and/or carbon dioxide, into a process for forming dimethyl ether wherein a dimethyl ether-containing product gas is formed,
setting a ratio of hydrogen to carbon monoxide weighted by the carbon dioxide concentration

$$\frac{c[H2] - c[CO2]}{c[CO] + c[CO2]}$$

of from 0.9 to 1.1 at the inlet of said process for forming dimethyl ether,
feeding said dimethyl ether-containing product gas to a process for converting dimethyl ether into olefins wherein an olefin-containing product gas is formed, and
separating olefins from said olefin-containing product gas by means of a separation process.

2. The process as claimed in claim 1, wherein said gas containing carbon monoxide and/or carbon dioxide is an off-gas from a steelworks comprising a blast furnace and/or a converter or from a smelting works.

3. The process as claimed in claim 1, wherein said gas containing carbon monoxide and/or carbon dioxide is an off-gas from a direct reduction process for iron ore are used.

4. The process as claimed in claim 1, wherein a ratio of hydrogen to carbon monoxide weighted by the carbon dioxide concentration $$\frac{c[H2] - c[CO2]}{c[CO] + c[CO2]}$$

of 1 is set at the inlet of said process for forming dimethyl ether.

5. The process as claimed in claim 1, wherein after said separating of olefins, the resultant gas is an alkane-containing tail gas, and said alkane-containing tail gas is fed as feed to a gas turbine for generating electric energy.

6. The process as claimed in claim 1, wherein hydrogen is separated off from said olefin-containing product gas by means of a cryogenic separation process.

7. The process as claimed in claim 1, wherein after said separating of olefins, the resultant gas is an alkane-containing tail gas, and said alkane-containing tail gas is fed into a process for the partial oxidation of alkanes to alkenes and alkynes in the presence of oxygen wherein an oxidation product gas is formed, and the oxidation product gas is recirculated to the separation process for separating olefins from said olefin-containing product gas.

8. The process as claimed in claim 7, wherein hydrogen is separated off from said olefin-containing product gas by means of a cryogenic separation process, and said hydrogen and said oxidation product gas are fed into a process for the catalytic hydrogenation of alkynes wherein a hydrogenation product gas is formed, and the hydrogenation product gas is recirculated to the separation process for separating olefins from said olefin-containing product gas.

9. The process as claimed in claim 1, wherein after said separating of olefins, the resultant gas is an alkane-containing tail gas, and said alkane-containing tail gas is fed to a thermal process in the absence of oxygen wherein a pyrolysis product gas and carbon are formed, and wherein said pyrolysis product gas is fed into a pressure swing absorption process where it is separated into hydrogen and an acetylene-containing tail gas.

10. The process as claimed in claim 1, wherein, upstream of the process for forming dimethyl ether, said offgas is fed into a process for reforming methane to form carbon monoxide thereby forming a reformer product gas.

11. The process according to claim 1, wherein, in said separating of olefins, ethylene and/or propylene are separated from said olefin-containing product gas by means of said separation process.

12. The process as claimed in claim 1, wherein after said separating of olefins, the resultant gas is an as alkane-containing tail gas, and methane is separated from said alkane-containing tail gas and fed to a gas turbine for generating electric energy.

\* \* \* \* \*